(12) United States Patent
Sharifi-Mehr et al.

(10) Patent No.: US 7,849,766 B2
(45) Date of Patent: Dec. 14, 2010

(54) SPEED MULTIPLY SCREWDRIVER HANDLE

(75) Inventors: Amir Ali Sharifi-Mehr, Bloomingdale, NJ (US); Andy Wonyong Choi, Wayne, NJ (US); Steven Krause, Oakland, NJ (US)

(73) Assignee: Stryker Spine (FR)

( * ) Notice: Subject to any disclaimer, the term of this patent is extended or adjusted under 35 U.S.C. 154(b) by 0 days.

(21) Appl. No.: 12/152,444

(22) Filed: May 14, 2008

(65) Prior Publication Data

US 2008/0282846 A1  Nov. 20, 2008

Related U.S. Application Data

(60) Provisional application No. 60/930,405, filed on May 16, 2007.

(51) Int. Cl.
*B25B 17/02* (2006.01)
*A61B 17/88* (2006.01)

(52) U.S. Cl. .......................... 81/57.3; 606/104
(58) Field of Classification Search .................. 81/57.3; 606/86 R, 104
See application file for complete search history.

(56) References Cited

U.S. PATENT DOCUMENTS

| | | | |
|---|---|---|---|
| 919,156 A | 4/1909 | Gilmore | |
| 2,477,528 A * | 7/1949 | Shrader | 475/270 |
| 2,756,792 A * | 7/1956 | Hirschman | 81/28 |
| 4,043,228 A * | 8/1977 | Venezio | 81/57.3 |
| 4,735,119 A * | 4/1988 | Riley | 81/57.3 |
| 4,846,027 A * | 7/1989 | Lu | 81/57.3 |
| 5,033,336 A * | 7/1991 | Chia-Tsai | 81/57.3 |
| 5,226,906 A * | 7/1993 | Crombie et al. | 606/916 |
| 5,406,866 A * | 4/1995 | Badiali | 81/57.3 |
| 5,613,585 A * | 3/1997 | Tiede | 192/43.1 |
| 5,924,339 A * | 7/1999 | Huang | 81/57.31 |
| 5,947,212 A * | 9/1999 | Huang | 173/216 |
| 6,189,422 B1 | 2/2001 | Stihl et al. | |
| 6,457,385 B1 * | 10/2002 | Hu | 81/57.3 |
| 6,602,260 B2 * | 8/2003 | Harari et al. | 606/104 |
| 6,681,660 B2 * | 1/2004 | Foard | 81/57.31 |
| 6,742,417 B2 * | 6/2004 | Ha | 81/57.36 |
| 7,168,340 B1 * | 1/2007 | Green | 81/57.3 |
| 2002/0096020 A1 * | 7/2002 | Hart et al. | 81/57.14 |
| 2005/0222575 A1 * | 10/2005 | Ciccone et al. | 606/104 |
| 2007/0043359 A1 * | 2/2007 | Altarac et al. | 606/61 |
| 2007/0239159 A1 * | 10/2007 | Altarac et al. | 606/61 |

OTHER PUBLICATIONS

International Search Report, PCT/US2008/06151.

* cited by examiner

*Primary Examiner*—David B Thomas
(74) *Attorney, Agent, or Firm*—Lerner, David, Littenberg, Krumholz & Mentlik, LLP

(57) ABSTRACT

A screwdriver is disclosed including a handle, a shaft, and a gearbox disposed between the handle and the shaft. The gearbox is structured and arranged to cause rotational motion of the shaft at a first rate due to rotational motion imparted on the handle at a second rate. In an embodiment, the first rate is greater than the second rate.

10 Claims, 1 Drawing Sheet

SPEED MULTIPLY SCREWDRIVER HANDLE

CROSS REFERENCES TO RELATED APPLICATIONS

The present application claims the benefit of the filing date of U.S. Provisional Application No. 60/930,405 filed May 16, 2007, the disclosure of which is incorporated herein by reference.

BACKGROUND OF THE INVENTION

Many orthopedic surgery procedures, particularly spinal surgery procedures, require surgeons to drive multiple screws into a patient's spine. During such delicate procedures, it is important for the surgeon to have a high degree of control and tactile feedback from any instrument used to drive the screws. This is important so that the necessary torque is applied to the screwdriver without overtightening the screws, which can damage the bone or the surrounding tissue and lead to injury or damage to the spinal cord. Moreover, control and feedback are useful to ensure that the screw is advanced properly into the bone, which includes maintaining the screw along the proper axial alignment.

Additionally, as in most surgeries, it is advantageous in spinal surgery that the procedure is performed as quickly as possible. Therefore, it is desirable to be able to advance the screws into the spine quickly. Automatic screwdrivers, including those which are driven by an electric motor or the like, are known for quickly driving screws. However, such devices do not provide much tactile feedback or control. Hand-driven screwdrivers are therefore preferred, despite lacking the speed advantage provided by automatic screwdrivers.

The design of screw threads has been altered as one possible solution to the problem of increasing the speed with which screws are advanced into bone, particularly during spinal surgery. For example, screws have been developed that include multiple, most frequently two, start threads. This arrangement allows for the threads to be positioned at a higher pitch, while maintaining the overall number of threads. The steeper pitch increases the speed at which the screw can be inserted into the bone by reducing the number of revolutions required in order to advance the screw by a given length. However, the steeper pitch of the threads may increase the likelihood of screw backout, which can be damaging to the tissue surrounding the spine and may lead to the instability of anything held in place by the screws.

It is therefore desired to provide an arrangement that provides the control and tactile feedback of a hand-driven screwdriver, while increasing the speed at which screws can be driven. Such a device should provide these advantages while being compatible with various types of screws, including those that have a single start thread.

SUMMARY OF THE INVENTION

An embodiment of the present invention relates to a screwdriver including a handle, a shaft, and a gearbox disposed between the handle and the shaft. The gearbox is structured and arranged to cause rotational motion of the shaft at a first rate due to rotational motion imparted on the handle at a second rate. In another embodiment, the first rate is greater than the second rate; however, yet other embodiments are contemplated wherein the first rate and the second rate are the same or wherein the first rate is less than the second rate.

The gearbox may additionally include an input gear, an output gear, a first connecting gear and a second connecting gear. The first connecting gear may engage the input gear and the second connecting gear may engage the output gear, the first and second connecting gears being fixed in rotational motion with respect to each other. The first and second connecting gears may be affixed to each other using a rod. In one embodiment, the gears are contained in a housing that is part of the gearbox.

The shaft of the screwdriver may include a screwdriver head formed integrally therewith for engaging a screw. Alternatively, the shaft of the screwdriver may include a quick-connect device for removably securing a screwdriver head to the shaft.

A further aspect of the present invention relates to a method of driving a screw. The method includes engaging a screwdriver with the screw, the screwdriver including a shaft adapted to engage with the screw, a handle, and a gearbox disposed between the handle and the shaft. The method further includes rotating the handle at a first rate, which causes the shaft to rotate at a second rate. In another embodiment, the second rate may be greater than the first rate. In yet another embodiment, the method is used to drive a bone screw into a bone of a patient, which may include a portion of a vertebrae. Such a method may be used in performing orthopedic surgery.

DETAILED DESCRIPTION

As used herein the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

Figure 1:
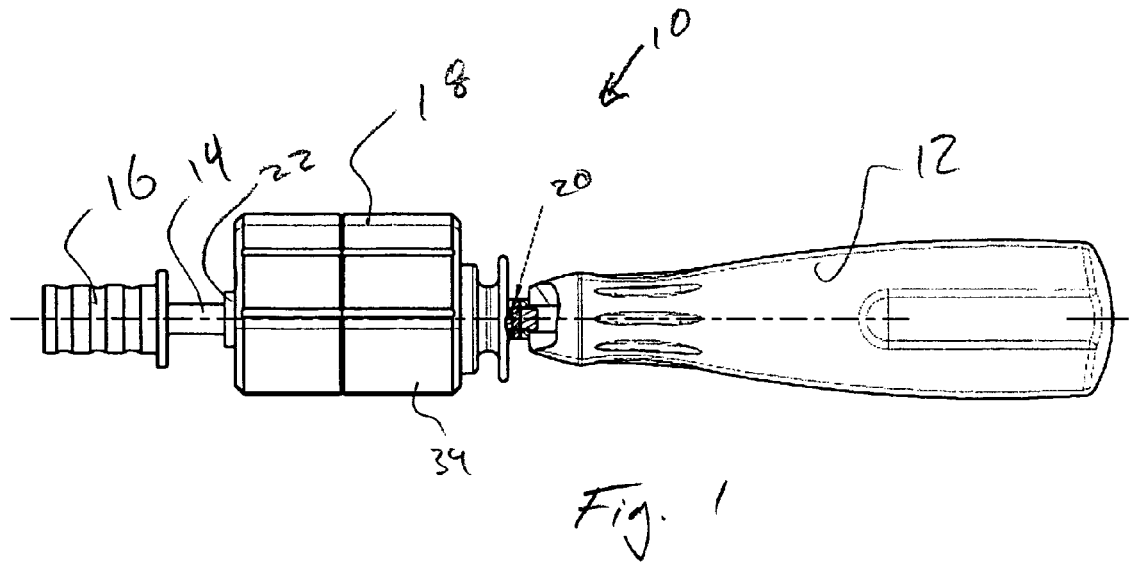
FIG. 1 is an elevation view of a screwdriver according to an aspect of the present invention.

Referring now to the drawings, where like reference numerals are used to indicate like features, there is shown in FIG. 1 a screwdriver 10 according to an embodiment of the present invention. Screwdriver 10 includes a handle 12 and a shaft 14. Handle 12 is located proximally of shaft 14. Further, the distal end of shaft may include a quick-connect device 16, as shown in FIG. 1, or it may include a screwdriver head integrally formed therewith. The quick-connect device 16 can be used to interchangeably attach one of several screwdriver heads, which are chosen based on application and to match the pattern on the screw used. Such interchangeable screwdriver heads can vary in size and type, including slotted, Philips, hex, etc. Such quick-connect devices are known along with the structure of the interchangeable screwdriver heads that are used in connection with the quick-connect device 16.

Handle 12 can be of any type typically used in a screwdriver. Such handles are typically in an elongate shape that is suitable for grasping with the hand, and may be contoured to better match the shape of the hand. The handle may also include ribs or other structures which enhance the grip of the user. Further the handle may be coated with rubber or the like to improve grip or the feel of the handle during use. Handle 12 may be made from plastic or metal. Further, handle 12 may be made from surgical-grade stainless steel, or other similar materials that can withstand the sterilization process that is necessary in order to reuse the screwdriver 10 in subsequent procedures.

Figure 2:
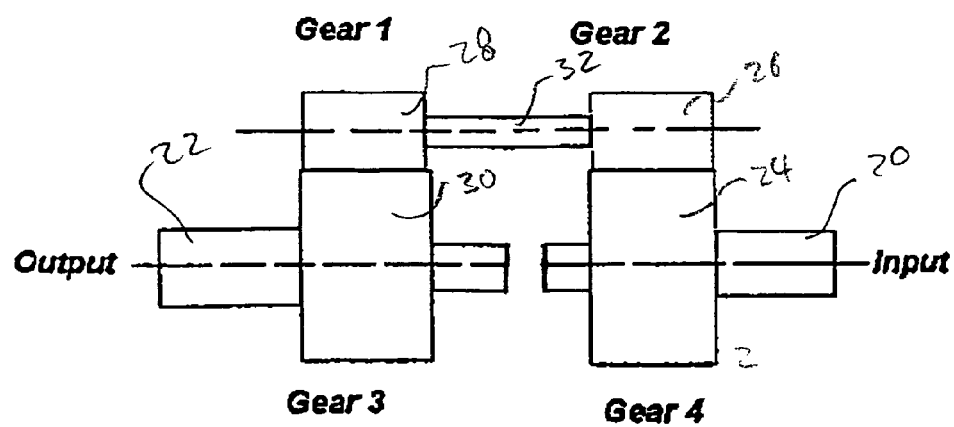
FIG. 2 is an elevation view of an exemplary gear mechanism that can be used in connection with a screwdriver according to an aspect of the present invention.

Gearbox 18 may be disposed between handle 10 and shaft 14 of screwdriver 10 and may include an input end 20 and an output end 22. Both input end 20 and output end 22 are connected to or integrally formed with handle 12 and shaft 14, respectively. In one embodiment, gearbox 18 may be structured and arranged to cause rotation of output end 22 based on rotation of input end 20 such that rate of rotation of the output end is different than the rate of rotation of the input end. For example, the rate of rotation of the output end may be faster than the rate of rotation of the input end. Alternatively, the rate of rotation of the output end may be slower than the rate of rotation of the input end. To achieve this, gearbox 18 may include a plurality of gears linking output end 22 and input end 20. For example, as shown in FIG. 2, input gear 24 is attached to input end 22 and output gear 30 is attached to output end 22. Further, input gear 24 and output gear 30 are linked by rod 32 which has a first gear 26 and a second gear 28 affixed thereto, and in one embodiment, on opposite ends thereof. First gear 26 is aligned with and meshes with input gear 24 and second gear 28 is aligned with and meshes with output gear 30. Accordingly, rod 32 links input gear 24 and output gear 30 such that, when rod 32 is held substantially stationary in position, while being allowed to rotate, rotation of input end 20 results in rotation of output end 22 in the same direction.

The relative rotational speed of output end 22 and input end 20 is influenced by the ratio in size of input gear 24 and output gear 30. In the arrangement shown in FIG. 2, if input gear 24 has a radius that is twice the radius of output gear 30, then output gear 30 will rotate at twice the speed of input end 20. As a further example, if input gear 24 has a radius that is half the radius of output gear 30, then output gear 30 will rotate at half the speed of input gear 24. Other gear arrangements are known or can be determined by one skilled in the art, and any suitable arrangement could be used in connection with gearbox 18 to achieve similar results.

Housing 34 of gearbox 18 may be structured to provide proper support for gears 24, 26, 28, 30 and any associated structures and features, including input end 20, output end 22, and rod 32. Housing 34 may also be structured to be grasped by the user of screwdriver 10 during use thereof.

In the embodiment of screwdriver 10 shown in FIG. 1, particularly when used in connection with the gear arrangement of FIG. 2, it may be necessary for the user of screwdriver 10 to hold gearbox 18 substantially stationary while rotating handle 12 in order to cause the desired rotation of shaft 14. In order to facilitate the holding of gearbox 18, housing 34 may be sized and shaped so as to provide an ergonomic shape to better fit within the hand of the user. Furthermore, as discussed above with respect to handle 12, housing 34 of gearbox 18 may include ribs or other features to improve the grip thereof. Additionally, the outside surface housing 34 may include rubber or the like to improve the comfort and grip thereof.

Gearbox 18 may further include a gear arrangement including multiple sets of gears which can be manipulated to achieve multiple ratios of rates of rotation between handle 12 and shaft 14 in a single device. Additionally, gearbox 18 can include a locking mechanism to lock the relative motion of input end 20 and output end 22. Such a mechanism can achieve this result by anchoring any one of gears 24, 26, 28, 30 to housing 34 or by anchoring two gears together such as first gear 24 and second gear 26, first gear 24 and fourth gear 30, or third gear 28 and fourth gear 30. Such a mechanism may further include a switch or lever (not shown) that projects from housing 34 such that it can be controlled by a user.

A variety of different gear ratios can be employed in connection with screwdriver 10. For example, input to output ratios in which input gear 24 is larger than output gear 30, such as 2:1, 2.5:1, 3:1, or the like, can be useful for increasing the speed at which the user of screwdriver 10 is able to effect rotation of screws which are driven, for example into bones of the spinal column. Such ratios can also improve the tactile feedback of the screwdriver by amplifying the subtle changes in frictional and other forces acting on the screw by the bone (or other substance) due to the reduced torque output between the input 20 and output 22 ends.

Gear ratios where the input gear 24 is smaller than the output gear 30, such as 1:2, 1:3, and the like, will cause a reduction in speed from the handle 16 to the shaft, but will increase the torque between the two ends. This makes it easier for the user to drive the screw, but reduces the rate at which the screw is driven.

A single screwdriver 10 can include gear arrangements in the form of a variable transmission system, which provides multiple gear ratios which can be selected by the user of the device as desired within a range of gear ratios. For example, gearbox 18 can include multiple gears which can be selectively engaged with input end 20 and output end 22 to provide a first arrangement selected such that output end 22 rotates faster than input end 20 and a second arrangement where output end 22 provides increased torque compared to input end 20. The selection of such gear arrangements can be controlled with a switch provided on the outside of housing 34 that can be manipulated by the user of screwdriver 10.

Another embodiment may be a method for driving a screw with a screwdriver, including engaging a screwdriver with a screw, wherein the screwdriver comprises a shaft adapted to engage the screw, a handle, and a gearbox and rotating the handle at a first rate, thereby causing the shaft to rotate at a second rate. The gearbox may include an input end attached to the handle and an output end attached to the shaft, the gearbox further including an input gear affixed to the input end, an output gear affixed to the output end, a first connecting gear and a second connecting gear connected to each other, the first connecting gear being operatively engaged with the input gear and the second connecting gear being operatively engaged with the output gear, the gears being arranged so as to cause rotational motion of the output end at a first rate due to rotational motion of the input end at a second rate.

Alternatively, a user may also use the variable transmission system such that a user may adjust the gear ratio, between the input gear and the output gear, throughout the method of driving the screw. For example, a user may choose a higher gear ratio, between the input gear and output gear, to increase the speed of the shaft relative to the handle, and a lower gear ration, between the input gear and output gear, to increase the amount of torque transmitted at the shaft end. Thus, in this example, a user may first use a lower gear ratio to start the driving of the screw, and then switch to a higher gear ratio to complete the driving of the screw more quickly. Of course, these selections may be used in reverse order, depending on the application.

Another method of using a screwdriver 10 according to various embodiments of the present invention involves either choosing one of a set of screwdrivers or one of a set of interchangeable screwdriver heads to match the screw to be used in accordance with the method. If a removable screwdriver head is used, it may be assembled with quick-connect device 16. The screwdriver head is then engaged with the screw and the handle 12 is turned using one hand while the other hand may hold gearbox 18 by its housing 34 so as to maintain gearbox 18 in a substantially stationary position. The rotation of handle 12 causes rotation of the shaft 14, which causes the screw to turn such that it is advanced into a hole. Screwdriver 10 may be arranged such that during such use, shaft 14 rotates at a faster rate than handle 12 resulting in faster advancement of the screw into the hole as compared to an ordinary screwdriver. In other embodiments, shaft 14 may rotate at a slower rate than handle 12 in order to provide increased torque when compared to an ordinary screwdriver.

In an alternate embodiment, one method of using a screwdriver 10 according to the present invention may include a method of using a screwdriver during a surgical procedure including gaining access to a bone inside a human body, engaging a screwdriver with a screw, wherein the screwdriver comprises a shaft adapted to engage the screw, a handle, and a gearbox, and rotating the handle at a first rate, thereby causing the shaft to rotate at a second rate, wherein the screw is driven into the bone at the second rate, wherein the gearbox comprises an input end attached to the handle and an output end attached to the shaft, the gearbox further including an input gear affixed to the input end, an output gear affixed to the output end, a first connecting gear and a second connecting gear connected to each other, the first connecting gear being operatively engaged with the input gear and the second connecting gear being operatively engaged with the output gear, the gears being arranged so as to cause rotational motion of the output end at a first rate due to rotational motion of the input end at a second rate.

In yet another embodiment, an alternative method for driving a screw with a screwdriver during a surgical procedure may include gaining access to a vertebrae, engaging a screwdriver with a screw, wherein the screwdriver comprises a shaft adapted to engage the screw, a handle, and a gearbox, and rotating the handle at a first rate, thereby causing the shaft to rotate at a second rate, wherein the screw is driven into the vertebrae at the second rate, wherein the gearbox comprises an input end attached to the handle and an output end attached to the shaft, the gearbox further including an input gear affixed to the input end, an output gear affixed to the output end, a first connecting gear and a second connecting gear connected to each other, the first connecting gear being operatively engaged with the input gear and the second connecting gear being operatively engaged with the output gear, the gears being arranged so as to cause rotational motion of the output end at a first rate due to rotational motion of the input end at a second rate.

In one embodiment of screwdriver 12, gearbox 18 includes a locking mechanism which locks the relative rotational motion of the gears within gearbox so that input end 20 and output end 22 rotate at the same rate. If such an embodiment is used, the user may advance the screw initially with the gearbox 18 in the unlocked position and may switch the gearbox 18 into the locked position as desired, for example, a user may lock the gearbox 18 when the screw is substantially advanced in order to provide increased torque or reduced speed (in embodiments when output end 22 rotates faster than input end 20 in the unlocked position) during tightening of the screw into position.

Although the invention herein has been described with reference to particular embodiments, it is to be understood that these embodiments are merely illustrative of the principles and applications of the present invention. It is therefore to be understood that numerous modifications may be made and are encouraged to be made to the illustrative embodiments without departing from the spirit and scope of the present invention as defined by the appended claims.

The invention claimed is:

1. A method for driving a screw with a screwdriver during a surgical procedure, comprising:
   Gaining access to a bone inside a human body;
   engaging a screwdriver with a screw, wherein the screwdriver comprises a shaft adapted to engage the screw, a handle, and a gearbox; and
   rotating the handle at a first rate, thereby causing the shaft to rotate at a second rate, wherein the screw is driven into the bone at the second rate,
   wherein the gearbox comprises an input end attached to the handle and an output end attached to the shaft, the gearbox further including an input gear affixed to the input end, an output gear affixed to the output end, a first connecting gear and a second connecting gear connected to each other, the first connecting gear being operatively engaged with the input gear and the second connecting gear being operatively engaged with the output gear, the gears being arranged so as to cause rotational motion of the output end at a first rate due to rotational motion of the input end at a second rate.

2. The method of claim 1, wherein the input gear is larger than the output gear.

3. The method of claim 1, wherein the input gear is smaller than the output gear.

4. The method of claim 1, wherein the input gear is the same size as the output gear.

5. The method claim 1, wherein the first connecting gear and second connecting gear are fixed in rotational motion with respect to each other.

6. The method of claim 5, wherein the first connecting gear and second connecting gear are affixed to one another with a rod.

7. The method of claim 1, wherein at least the input gear, output gear, first connecting gear and second connecting gear are contained within a housing.

8. The method of claim 1, wherein the screwdriver further comprises a screwdriver head formed integrally on a distal end of the shaft.

9. The method of claim 1, wherein the screwdriver further comprises a quick-connect device for removably securing a screwdriver head to a distal end of the shaft.

10. A method for driving a screw with a screwdriver during a surgical procedure, comprising:
   Gaining access to a vertebrae;
   engaging a screwdriver with a screw, wherein the screwdriver comprises a shaft adapted to engage the screw, a handle, and a gearbox; and
   rotating the handle at a first rate, thereby causing the shaft to rotate at a second rate, wherein the screw is driven into the vertebrae at the second rate,
   wherein the gearbox comprises an input end attached to the handle and an output end attached to the shaft, the gearbox further including an input gear affixed to the input end, an output gear affixed to the output end, a first connecting gear and a second connecting gear connected to each other, the first connecting gear being operatively engaged with the input gear and the second connecting gear being operatively engaged with the output gear, the gears being arranged so as to cause rotational motion of the output end at a first rate due to rotational motion of the input end at a second rate.

* * * * *